(12) United States Patent
Yaniv

(10) Patent No.: US 7,674,628 B2
(45) Date of Patent: Mar. 9, 2010

(54) REMOTE IDENTIFICATION OF EXPLOSIVES AND OTHER HARMFUL MATERIALS

(75) Inventor: Zvi Yaniv, Austin, TX (US)

(73) Assignee: Applied Nanotech Holdings, Inc., Austin, TX (US)

( * ) Notice: Subject to any disclaimer, the term of this patent is extended or adjusted under 35 U.S.C. 154(b) by 616 days.

(21) Appl. No.: 11/500,669

(22) Filed: Aug. 8, 2006

(65) Prior Publication Data

US 2010/0022009 A1    Jan. 28, 2010

Related U.S. Application Data

(63) Continuation-in-part of application No. 10/633,335, filed on Aug. 1, 2003.

(60) Provisional application No. 60/706,547, filed on Aug. 9, 2005.

(51) Int. Cl.
*G01N 21/00* (2006.01)
(52) U.S. Cl. .................................................. 436/164
(58) Field of Classification Search ................. 436/164
See application file for complete search history.

(56) References Cited

U.S. PATENT DOCUMENTS

| 4,740,086 | A | 4/1988 | Oehler et al. |
| 5,457,073 | A | 10/1995 | Ouellet ............... 438/624 |
| 5,615,043 | A | 3/1997 | Plaessmann et al. |
| 5,990,479 | A | 11/1999 | Weiss et al. ............... 250/307 |
| 6,261,779 | B1 | 7/2001 | Barbera-Guillem et al. ..... 435/6 |
| 6,380,550 | B1 | 4/2002 | Canham et al. |
| 6,458,327 | B1 | 10/2002 | Vossmeyer ............... 422/68.1 |
| 6,530,944 | B2 | 3/2003 | West et al. ............... 607/88 |
| 6,537,755 | B1 | 3/2003 | Drmanac ............... 435/6 |
| 6,544,732 | B1 | 4/2003 | Chee et al. ............... 435/6 |
| 6,692,031 | B2 | 2/2004 | McGrew ............... 283/93 |
| 6,778,165 | B2 | 8/2004 | Hubby et al. ............... 345/107 |
| 6,797,944 | B2 * | 9/2004 | Nguyen et al. ............... 250/286 |
| 6,908,737 | B2 | 6/2005 | Ravkin et al. ............... 435/6 |
| 6,929,950 | B2 | 8/2005 | Canham et al. |

(Continued)

FOREIGN PATENT DOCUMENTS

WO    WO 2005111559 A2 * 11/2005

OTHER PUBLICATIONS

Carr, J.; "Instrumentation." Tessella Scientifica Software Solutions. Issue V1 R1.M1. Apr. 2003.*

(Continued)

*Primary Examiner*—Walter D Griffin
*Assistant Examiner*—Bobby Ramdhanie
(74) *Attorney, Agent, or Firm*—Kelly Kordzik; Matheson Keys Garsson & Kordzik PLLC

(57) ABSTRACT

Embodiments of the present invention are generally directed to the remote detection of explosives and other harmful materials. In some such embodiments, such remote detection involves the use of semiconducting nanoparticles. In some or other such embodiments, such remote detection involves the use of photoacoustic detection and/or spectroscopy. In some such latter embodiments, the photoacoustic system comprises a light source 201 that passes through a chopper 202 and into a photoacoustic cell 203 comprising the analyte gas. Pressure waves within the cell are detected as sound waves by microphones 204. The signal produced by the microphones can then be amplified and transmitted to a remote location, typically via a wireless means.

20 Claims, 2 Drawing Sheets

U.S. PATENT DOCUMENTS

| | | | |
|---|---|---|---|
| 2002/0004246 A1 | 1/2002 | Daniels et al. | 436/514 |
| 2003/0013091 A1 | 1/2003 | Dimitrov | 435/6 |
| 2004/0009911 A1 | 1/2004 | Harris et al. | 514/12 |
| 2004/0166319 A1 | 8/2004 | Li et al. | |

OTHER PUBLICATIONS

Kreuzer, L. B. "Ultralow Gas Concentration Infrared Absorption Spectrioscopy." *Journal of Applied Physics*, 1971, 42(7), pp. 2934-2943.*

Harshbarger, W. R.; Robin, M. B. "The Opto-Acoustic Effect: Revival of an Old Technique for Molecular Spectroscopy." *Accounts of Chemical Research*, 1973, 6(10), pp. 329-334.*

Kreuzer, L.B.; Petal, C. K. N. "Reports: Nitric Oxide Air Pollution: Detection by Optoacoustic Spectroscopy." *Science*, 1971, 173 (3991), pp. 45-47.*

Anaple, G., et al., "Molecular structure of porous Si," *J. Appl. Phys.* 78 (6), pp. 4273-4275. Sep. 15, 1995.

Heinrich, J., et al., "Luminescent Colloidal Silicon Suspensions from Porous Silicon," *Science*, vol. 255, pp. 66-68. Jan. 3, 1992.

Credo, G.M., et al., "External quantum efficiency of single porous silicon nanoparticles," *Applied Physics Letters*, vol. 74, No. 14, pp. 1978-1980. Apr. 5, 1999.

Mason, et al., "Luminescence of Individual Porous Si Chromophores," *Physical Review Letters*, vol. 80, No. 24, pp. 5405-5408. Jun. 15, 1998.

Singh, et al., "Quenching and recovery of photoluminescence intensity of silicon nanoparticles embedded in optically transparent polymers," *Semicond. Sci. Technol.*, vol. 17, No. 10, pp. 1123-1127. Sep. 20, 2002.

Tsuo, et al., "Environmentally Benign Silicon Solar Cell Manufacturing," Presented at the $2^{nd}$ World Conference and Exhibition on Photovoltaic Solar Energy Conversion, Jul. 6-10, 1998. Vienna, Austria. (7 pages).

International Searching Authority: Notification of Transmittal of the International Search Report and the Written Opinion of the International Searching Authority for International Application No. PCT/US 06/31230, mailed Sep. 15, 2008 (10 pages).

P. Przybylowicz et al., *Black and Smokeless Powders, Technologies for Finding Bombs and the Bomb Makers*, National Academy Press. Washington D.C. 1998, 164 pp.

* cited by examiner

REMOTE IDENTIFICATION OF EXPLOSIVES AND OTHER HARMFUL MATERIALS

CROSS REFERENCE TO RELATED APPLICATIONS

The present application is a Continuation-in-Part of U.S. patent application Ser. No. 10/633,335, filed Aug. 1, 2003 and which claims the benefit of U.S. Provisional Patent Application 60/400,784 filed Aug. 2, 2002. Additionally, the present application claims priority to U.S. Provisional Patent Application 60/706,547, filed Aug. 9, 2005.

TECHNICAL FIELD

The present invention relates in general to chemical detection and sensing, and in particular, to exploiting the photoluminescence properties of nanometer-size particles for chemical and hazardous materials detection and/or to the use of photoacoustic detection systems for the remote detection of such chemical and hazardous materials.

BACKGROUND INFORMATION

"Markers" or "taggants" are terms used to represent any material that can be added to explosives, chemical weapons, etc. in order to assist in identifying the explosive/weapon or its source before, after, or both before and after its detonation or use. While the motive for including such markers or taggants in explosives and other weapons is clearly anti-terrorism, taggants have also been proposed as anti-counterfeiting devices, anti-tampering devices, and as quality control devices in commercial products ranging from gasoline to perfumes ("Black and Smokeless Powders: Technologies for Finding Bombs and the Bomb Makers," Committee on Smokeless and Black Powder, National Research Council, 1998).

While such markers or taggants can aid authorities in their investigation of detonated explosives or deployed chemical weapons and in identifying the source of such seized weapons, they generally cannot prevent the harmful agent from being used. Furthermore, the taggants must be inserted during the production of the harmful agent. This means that weapons or other harmful devices fabricated by terrorist elements or rogue nations would likely be unidentifiable.

One way of overcoming the above-mentioned limitations is to devise strategies for chemically sensing explosives, chemical weapons, and other harmful agents by exploiting the high vapor pressures that many of them possess and the emission of nitrogen- and phosphorus-containing free radicals from the explosives, chemical weapons, and other harmful agents. This is the case for phosphorus-containing chemical nerve agents like sarin, soman, tabun, and VX and for nitro-containing explosives like trinitrotoluene (TNT) and nitroglycerine. Chemical sensing, such as utilizing spectral characteristics, could be used to detect such harmful materials in public places like airports, subways, shopping malls, etc. This would allow for the pre-emptive identification of harmful materials, before they have inflicted any damage.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
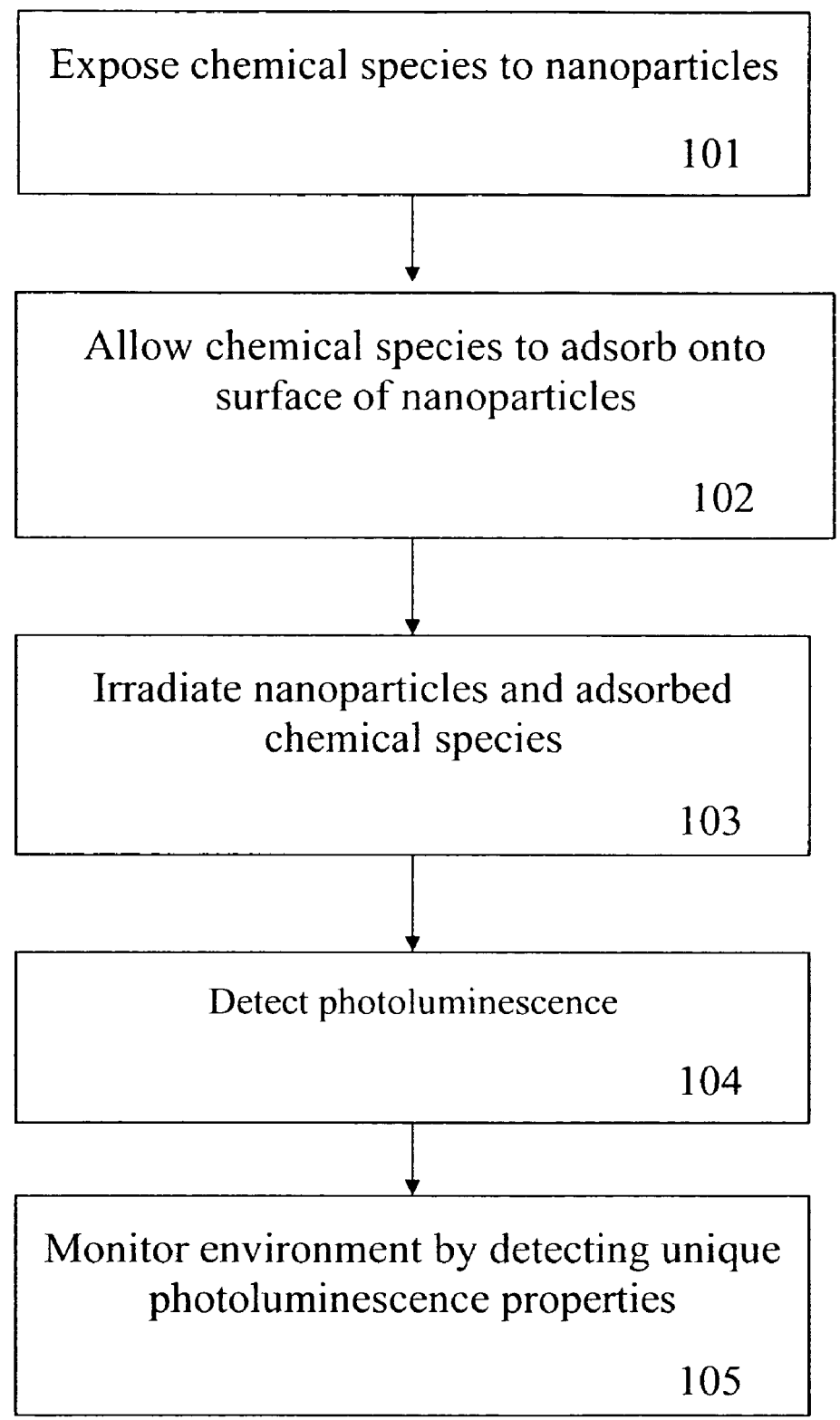
FIG. 1 illustrates, in general terms, a process of using nanoparticles for chemical sensing.

Embodiments of the present invention are generally directed to the remote detection of explosives and other harmful materials. In some such embodiments, such remote detection involves the use of semiconducting nanoparticles. In some or other such embodiments, such remote detection involves the use of photoacoustic detection and/or spectroscopy.

Nanoparticle-Based Detection

For semiconductors, electronic excitations take the form of electron-hole pairs called excitons. Quantum confinement is a phenomenon which occurs when a semiconductor particle's size is decreased below its excitonic Bohr radius, which is generally in the 10 to 50 nanometer (nm) range, but is different for each material. If one imagines a shrinking semiconductor particle, at the quantum confinement threshold, the semiconductor's bandgap begins to increase. As the particle continues to get smaller, the bandgap continues to increase, but the valance and conduction bands begin to separate into discreet energy levels reminiscent of molecular orbitals.

In addition to an increased bandgap, quantum-confined particles, or "quantum dots," possess interesting photoluminescent behavior as well. This is due to the fact that electronic transitions previously unallowed in the bulk state, may suddenly become allowed in the quantum confined state. By careful control of the particle size, the bandgap and photoluminescence (PL) properties can be tuned to yield materials with unique optical properties and spectral characteristics.

In some embodiments, the present invention comprises a process of using nanometer-size particles (also known as nanoparticles or nanocrystals, according to the present invention), in the sensing and identification of chemicals and harmful agents by exposing such chemicals and harmful agents to the nanoparticles. Such exposure could be in the gas phase, the liquid phase, or the solid phase, and could include mixed phase exposures. Such sensing would exploit unique properties of the nanoparticles, specifically unique photoluminescence properties of the nanoparticles.

Nanoparticles, according to the present invention, are particles comprising finite bandgap materials, and having particle diameters which are generally less than about 100 nm. Finite bandgap materials, in contrast to zero bandgap and infinite bandgap materials, can be categorized as semimetals, semiconductors, insulators, and combinations thereof. Examples of finite bandgap materials include, but are not limited to, silicon (Si), gallium arsenide (GaAs), cadmium sulfide (CdS), cadmium selenide (CdSe), titanium dioxide ($TiO_2$), diamond, cerium oxide ($CeO_2$), silicon oxide ($SiO_2$), aluminum oxide ($Al_2O_3$), and the like and combinations thereof.

Photoluminescence (PL), according to the present invention, comprises all forms of luminescence including fluorescence, phosphorescence, and combinations thereof. The excitation radiation, which induces photoluminescence, is typically in the ultraviolet (UV) region of the electromagnetic (EM) spectrum, but can generally be in any or all regions of the electromagnetic spectrum capable of inducing photoluminescence in the nanoparticles. Photoluminescence, according to the present invention, is typically in the visible (optical) region of the electromagnetic spectrum, but can generally be in any or all regions of the electromagnetic spectrum.

Photoluminescence of the nanoparticles, according to a process of the present invention, is induced when the nanoparticles are irradiated with light, particularly with wavelengths found in the UV region of the electromagnetic spectrum. The emitted radiation (the photoluminescence) is generally in the visible (optical) region of the electromagnetic spectrum. When a chemical species adsorbs onto the surfaces of the nanoparticles, the photoluminescence properties of the nanoparticles are altered. Chemical sensing is accomplished by detecting and, in some embodiments, analyzing the altered photoluminescence properties. Sensing, according to the present invention, includes, but is not limited to, detecting, analyzing, monitoring, and the like and combinations thereof.

In some embodiments of the present invention, the nanoparticles comprise quantum confined particles, wherein the bandgap of said quantum confined particles has been increased (in terms of energy) relative to the bulk material.

In some embodiments of the present invention, the nanoparticles are chemically functionalized prior to their use in chemical sensing. Such functionalization broadens the range in which the nanoparticles' photoluminescence properties can be tuned, and it can vary the efficiency with which chemical species can be adsorbed onto the nanoparticle surface.

In some embodiments of the present invention, the nanoparticles comprise silicon nanoparticles.

Nanoparticles, according to a process of the present invention, can be made by any known technique which suitably provides particles which reliably photoluminescence in the manner described herein. Such nanoparticles range generally in size from about 1 nm to about 100 nm, specifically from about 1 nm to about 50 nm, and more specifically from about 1 nm to about 10 nm. For any given application utilizing a quantity of nanoparticles, such nanoparticles have a size variation of generally up to about 20 nm, specifically up to about 10 nm, and more specifically up to about 3 nm.

In general terms, a process of the present invention comprises of a number of steps. Referring to FIG. 1, nanoparticles (e.g., silicon nanoparticles) of a specific particle size and/or range of sizes having initial photoluminescence properties are exposed to a chemical species of interest in a controlled environment 101 (e.g., 25° C., 1 atm of $N_2$). For example, the initial photoluminescence properties can be the photoluminescence properties that the nanoparticles exhibit when initially produced. Also, for example, the initial photoluminescence properties can be the photoluminescence properties that the nanoparticles exhibit after initial production, any further processing (such as, but not limited to, combining the nanoparticles with a dispersant or the like such as an aerosol) and exposure to a controlled environment, but before contact with a chemical species of interest in the controlled environment. Exposure occurs such that the chemical species of interest adsorbs onto the surface of the nanoparticles 102. The nanoparticles with the adsorbate present are irradiated with radiation (e.g., UV light) of a given frequency or frequencies 103. Emitted radiation (photoluminescence) is then detected and analyzed 104 with a device, such as, but not limited to, a spectrometer, to determine how the photoluminescence properties of the nanoparticles have been altered (e.g., shifted) relative to the initial photoluminescence properties of the nanoparticles in the same environment but with the absence of the particular chemical species of interest to provide for a pre-defined altered photoluminescence property or properties that corresponds to the particular chemical species of interest. The chemical species of interest can then be detected in an environmental setting by monitoring for altered photoluminescence properties and comparing the altered photoluminescence properties to the pre-defined altered photoluminescence properties 105. Thus, an environment can be monitored for a particular species of interest by looking for a particular change (i.e., monitoring for a specific frequency or frequencies) in the photoluminescence behavior of the nanoparticles and comparing to the pre-defined altered photoluminescence properties.

Exposing, as referred to herein, comprises any time period, temperature, pressure, and atmosphere that suitably provides for the chemical species of interest to adsorb onto the surface of the nanoparticles according to a process of the present invention as described herein. Exposing generally includes a temperature generally in the range of from about $-20°$ C. to about $+200°$ C., a pressure generally in the range of from about 1 millitorr to about $1 \times 10^5$ torr, a time period generally in the range of from about 1 millisecond to about 10 hours, and a controlled atmosphere. A controlled atmosphere includes, but is not limited to, nitrogen, hydrogen, argon, oxygen, air, fluorocarbons, chlorofluorocarbons, helium, and the like and combinations thereof.

In some embodiments of the present invention, the steps outlined above are carried out for a number of chemical species of interest, thereby creating a database of photoluminescence shifts, and increasing the number of chemical species which can be detected. Sensing, according to the present invention, can thus determine the presence and identity of one or more unknown chemical species.

In some embodiments of the present invention, the adsorption of a chemical species of interest onto the surfaces of the nanoparticles is a reversible process. In other embodiments, the adsorption is essentially non-reversible. Adsorption, according to the present invention, includes, but is not limited to, physisorption, chemisorption, and combinations thereof.

In some embodiments of the present invention, a controlled environment comprises a self-contained box or room.

In some embodiments of the present invention, irradiation of the nanoparticles with UV radiation is done with a UV laser.

In some embodiments of the present invention, the photoluminescence is detected and/or analyzed by an optical detection method. Optical detection methods include, but are not limited to, wavelength selective detectors.

In some embodiments of the present invention, the photoluminescence is detected and/or analyzed by a spectrometer. In other embodiments, optical filters are employed.

In some embodiments of the present invention, an optical amplifying device (e.g., a photomultiplier tube) is used to increase the sensitivity of the sensing by several orders of magnitude.

In some embodiments of the present invention, the concentration of the chemical species of interest can be determined and/or monitored. These embodiments rely on a calibration of the photoluminescence change in the nanoparticles with known chemicals of known concentration.

In some embodiments of the present invention, the chemical species of interest (the object of the sensing) is a harmful agent. Harmful agents, according to the present invention, include, but are not limited to, toxins, carcinogens, mutagens, lachrymators, flammable species, nerve agents, explosives, and the like and combinations thereof.

In some embodiments of the present invention, the decomposition products of the actual species of interest are being sensed, such as detecting explosives, chemical weapons, and other harmful agents. Such species often contain nitrate and phosphate moieties. Slow decomposition results in nitrogenand phosphorus-containing free radicals being emitted. These products of decomposition can, at times, be more easily detected by the present invention than the actual species of interest.

In an embodiment of the present invention, harmful materials would be detected by spraying a suspect item (e.g., luggage or mail) with an aerosol of nanoparticles (e.g., silicon nanoparticles) having one or more pre-defined altered photoluminescence properties, illuminating the suspect item with a UV laser in the process of spraying it with the aerosol of nanoparticles, measuring the photoluminescence shift or change, i.e., measuring the altered photoluminescence properties, and observing whether or not there is a pre-defined shift or change in the photoluminescence spectra corresponding to a known—and already evaluated—chemical agent (sarin, for example), i.e., comparing the altered photoluminescence properties to the one or more pre-defined altered photoluminescence properties. Such a process could be carried out remotely from a distance. In the case of sarin, the high vapor pressure of this nerve agent might render the environment in the immediate vicinity of the article to be relatively high in sarin content—even if it were enclosed in some type of crude container that permitted the escape of merely trace amounts. The sarin vapor would then cause a predetermined shift or change in the photoluminescence spectra of the nanoparticles on account of the altered chemical environment. A variation on this embodiment would be to use the nanoparticle aerosol in the vicinity of a military weapons depot, whereby leaks in containers containing explosives and chemical weapons could be detected and identified.

Another embodiment of the present invention would comprise flooding a room (or a public place where there are people present) with nanoparticles of the present invention, exposing such nanoparticles to UV radiation, and monitoring their photoluminescence properties. In such an embodiment, care must be taken to ensure that the nanoparticles are non-toxic. In the event that an explosive or chemical agent was introduced into the room, a pre-defined shift or change in the photoluminescence spectrum of the nanoparticles would be observed corresponding to the particular harmful agent introduced into the room, e.g., the nanoparticles would exhibit altered photoluminescence properties that could be compared to one or more pre-defined altered photoluminescence properties. Identification of harmful agents in such a manner would likely permit their containment before they caused devastating effects.

Variations on the above-mentioned embodiments would be the detection of residues of harmful agents on the clothing or hands of individuals. Thus, an individual who merely came into contact with such agent could be identified.

Identification of agents as described herein need not be limited to screening techniques, however. By a having pre-defined knowledge of how a particular harmful agent alters the chemical environment of the nanoparticles and alters the photoluminescence properties of the nanoparticles (and how it shifts the corresponding photoluminescence spectrum), it is possible to use solutions of these nanoparticles in forensic laboratories to identify harmful agents.

Another embodiment of the present invention would include using nanoparticles of the present invention as traditional markers or taggants in explosives, chemical weapons, and other harmful agents. Since the taggants must possess some unique property (e.g., radioactivity, isotopic abundance, etc.), the unique photoluminescence properties of the nanoparticles should be suitable for such a role. While this embodiment may not permit pre-emptive detection of such agents, nanoparticles may prove superior to traditional taggants, especially in that their optical properties can be tuned by slight variations in their size. Other variations of this embodiment would include the use of nanoparticles as taggants for anti-counterfeiting, anti-tampering, and anti-piracy purposes. Thus, their inclusion in currency, books, software, music CDs, etc. is envisioned. Because their optical properties are tunable, they may be more difficult for unauthorized parties to replicate and counterfeit.

Photoacoustic-Based Methods

In some embodiments, the present invention is directed to methods of remotely-detecting/identifying explosives and other harmful chemical species using photo-acoustic techniques. Photoacoustic techniques have a number of advantages such as a very strong signal-to-noise ratio, and can be tuned to very specifically detect the explosive materials with sensitivities in the range of about 1 part per million (ppm) to approximately 1 part per billion (ppb) in certain situations such as for plastic explosives.

Such above-described embodiments generally involve a process comprising the steps of: (a) irradiating an environmental region potentially comprising a deleterious chemical species (e.g., an explosive, a carcinogen, a nerve agent, etc.); (b) locally detecting any such chemical species potentially present with a photoacoustic means and producing a signal comprising information regarding the presence of such deleterious chemical species; and (c) transmitting the signal to a remote location.

Remote detection, as it relates to the use of photoacoustic detection systems, means that the detection is carried out in a region that is isolated either spatially or physically from the observer(s), i.e., those individuals carrying out the detection. The level or type of isolation is dependent upon the nature of the potential hazards associated with the deleterious species potentially present in the environment in question. Generally, however, such isolation will provide at least the minimum amount of protection required to ensure the safety of those performing the detection. In some embodiments, such isolation can be provided by providing a physical barrier (e.g., a closed glass environment) between the environmental region potentially comprising a deleterious chemical species and the observer. In some or other embodiments, such isolation is provided by having the observer a sufficient distance to ensure such safety. Depending on the nature of the potential hazard, this could be anywhere from a meter or so to several kilometers or more.

The use of such photoacoustic processes in such above-described remote sensing applications can have numerous variations. For example, in some embodiments, a photoacoustic detector is installed in location of interest and then the signal is wirelessly transmitted to a remote location when a certain gas/species is detected. In some or other embodiments, if wireless transmission is prohibited due to certain limitations in the field or in the area of interest, a tunable UV laser can interrogate the photoacoustic cavity from a large distance by tuning the laser to specific well-defined frequencies with which the photoacoustic effect can be triggered and a specific gas identified. Devices using the photoacoustic effect in such a way can be easily miniaturized, and one can envision portability and even distribution of the device to individual soldiers in the field. In some or other such embodiments, in a way that is somewhat analogous to the way microwaves are used, Applicants believe that this photoacoustic phenomena can be used without a dedicated cavity by shining an infra-red (IR) laser on an area of interest and then trying to listen to the specific acoustic effect with the help of special remotely-located microphones. Further, shining a laser beam for a dedicated gas on an area of interest and comparing it to the beam reflected from an area in the vicinity that does not contain the specific gas in question and then comparing the two reflected beams, the presence of the harmful gas can be detected and the signal-to-noise ratio can be increased.

One of the specific photoacoustic methods capable of detecting outgassed by-products or vapors of explosive materials is photoacoustic spectroscopy (PAS). Initially discovered by Alexander Bell in 1880, this method was further developed theoretically by Rosencwaig and Gersho in 1973. The idea behind the photoacoustic effect is based on the detection of sound waves produced by a gas surrounding an object which absorbs the light from a light source modulated by amplitude. The object can be in a solid state, liquid, or gas phase. A schematic diagram of an exemplary PAS detection system is shown in FIG. 2.

Figure 2:
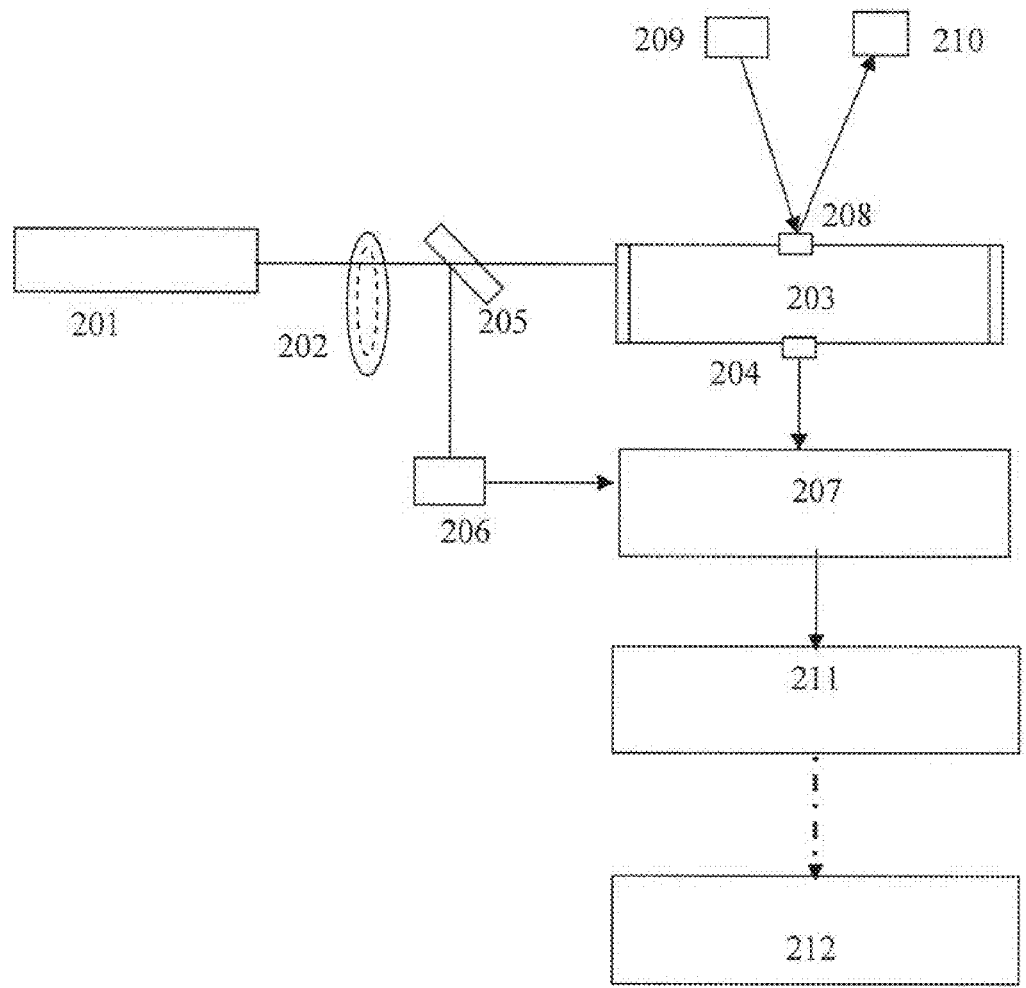
FIG. 2 depicts a photoacoustic detection system useful for remote sensing of chemical and hazardous materials, in accordance with some embodiments of the present invention.

Referring to FIG. 2, the light beam from light source 201 passes through the chopper 202 into a photoacoustic cell 203. The photoacoustic cell for gas spectroscopy is designed as an optical resonator to allow multi-pass light propagation within the cell. The cell has an inlet and outlet for gas sampling. When the gas in the cell absorbs the light from the light source, it will heat up due to non-radiative transitions from excited to the ground state. If the light beam is further modulated by the chopper, it will produce periodic pressure waves within the cell that are detected as sound waves by microphones 204. The electrical signal from microphones is amplified by a lock-in amplifier 207 using a reference signal from a photodetector 206 in order to improve the system sensitivity and the signal-to-noise ratio. The signal may be amplified by amplifier 211, and transmitted to a remote location 212 by electrical transmission over a wire, wireless radiofrequency transmission, or optical transmission. The light source typically comprises a source of white light and a monochromator. Scanning the monochromator over a desired spectrum range, it is possible to measure the optical absorption of the spectrum of a sample.

Most gases or vapors of organic substances have absorption lines in the infrared (IR) range of spectrum. This relates also to $NO_2$ group which are present in almost all explosives. Table 1 shows the structures, chemical formulae and vapor pressures of different explosive materials.

approach to produce a narrow-band IR radiation is to use optical filters with a broadband light source. Other approaches use IR lasers emitting at a wavelength at or near the absorption line maximum.

To make the system respond selectively to different gases, the light source 210 can be tunable in light wavelength (or corresponding frequency) so that the optical absorption line maximum $\lambda_a$ lies within the tuning range. In this case, if the light wavelength changes from $\lambda_a-\delta\lambda$ to $\lambda_a+\delta\lambda$, the sound intensity will have a peak while the light wavelength equals to $\lambda_a$, and the sound intensity will be low as the wavelength will approach $\lambda_a\pm\delta\lambda$.

In some or other embodiments, the photoacoustic detection system can use, instead of a microphone, a mirror that can vibrate at a frequency of light modulation. In this case, no electrical system is needed for sound detection. Instead, another laser 209 can be used that shines the light onto a mirror 208, and the response is measured by a dual position-sensitive photodetector 210.

Another embodiment uses a retroreflector, instead of the photoacoustic cell, in which one of the three mirrors is mounted on a cantilever and has a mechanical resonance at a frequency of light modulation. The same detection system (i.e., parts 208-210) can be used for measuring the response from the gases or vapors that surround the retroreflector.

Although the present invention has been described with respect to specific embodiments, the details thereof are not to be construed as a limitation, for it will be apparent to those of skill in the art that various embodiments, changes and modifications may be resorted to without departing from the spirit and scope thereof, and it is understood that such equivalent embodiments are intended to be included within the scope of the present invention.

What is claimed is:

1. A process comprising the steps of:
   a) exposing a deleterious chemical species to nanoparticles such that said chemical species adsorbs onto a surface of the nanoparticles as a chemical adsorbate;
   b) irradiating the nanoparticles comprising the adsorbed deleterious chemical species;

TABLE 1

| Explosive | Nitroglycerin | TNT | PETN | RDX | Tetryl | HMX |
|---|---|---|---|---|---|---|
| CAS No. | 55-63-0 | 118-96-7 | 78-11-5 | 121-82-4 | 479-45-8 | 2691-41-0 |
| Formula | $C_3H_5O_3(NO_2)_3$ | $C_7H_5(NO_2)_3$ | $C_5H_8O_4(NO_2)_4$ | $C_3H_6N_3(NO_2)_3$ | $C_7H_5N(NO_2)_4$ | $C_4H_8N_4(NO_2)_4$ |
| Weight | 227.1 | 227.1 | 316.1 | 222.1 | 287.1 | 296.2 |
| Vapor Pressure | $4 \times 10^{-3}$ | $5.5 \times 10^{-6}$ | $12 \times 10^{-9}$ | $4.1 \times 10^{-9}$ | $0.4 \times 10^{-9}$ | $3.33 \times 10^{-14}$ |
| Structure | | | | | | |

All the above-listed explosives contain three or four $NO_2$ groups in their molecular structure. It is convenient for detection of all these molecules to have a technique that detects the common $NO_2$ groups. The absorption lines of $NO_2$ are observed in mid-IR range, having wave numbers of 1350 and ~1530 cm$^{-1}$, and require an IR source for their detection. One c) locally detecting the adsorbed chemical species with a photoacoustic means and producing a signal comprising information regarding the presence of such chemical species; and d) transmitting the signal to a remote location.

2. The process of claim 1, wherein the deleterious chemical species is selected from the group consisting of explosives, nerve agents, carcinogens, and combinations thereof.

3. The process of claim 1, wherein the deleterious chemical species comprises at least one nitro ($-NO_2$) functionality.

4. The process of claim 1, wherein the photoacoustic means physically samples the adsorbed deleterious chemical species.

5. The process of claim 1, wherein the photoacoustic means involves photoacoustic spectroscopy.

6. The process of claim 1, wherein the step of irradiating involves a laser source.

7. The process of claim 5, wherein the step of irradiating involves a source of white light and a scanning monochrometer.

8. The process of claim 1, wherein the step of irradiating involves a source of infrared radiation.

9. The process of claim 1, wherein the signal further comprises information about the type of chemical species.

10. The process of claim 1, wherein the signal further comprises information about the concentration of the chemical species.

11. The process of claim 1, wherein the remote location is separated from the local environmental region by a separation means selected from the group consisting of a distance of at least 1 meter, a physical barrier, and combinations thereof.

12. The process of claim 1, wherein the signal is transmitted via a method selected from the group consisting of (a) electrical transmission over a wire, (b) wireless radiofrequency transmission, and (c) optical transmission.

13. The process of claim 5, wherein the photoacoustic spectroscopy comprises a photoacoustic cell for gas spectroscopy that is designed as an optical resonator to allow multi-pass light propagation within the cell.

14. A process comprising the steps of:
   a) exposing an explosive material to nanoparticles such that said explosive material adsorbs onto a surface of the nanoparticles as a chemical adsorbate;
   b) irradiating the nanoparticles comprising the adsorbed explosive material with infrared radiation;
   c) locally detecting the adsorbed explosive material with a photoacoustic detection system comprising at least one microphone so as to produce a signal comprising information regarding the presence of such explosive material; and
   d) transmitting the signal wirelessly to a location separated from the environmental region of interest by way of a separation means selected from the group consisting of a physical barrier, a distance of at least one meter, and combinations thereof.

15. The process of claim 14, wherein the explosive material comprises at least one nitro ($-NO_2$) functionality.

16. The process of claim 14, wherein the source of infrared radiation is an infrared laser.

17. The process of claim 14, wherein the physical barrier allows transmission of radiation of some regions of the electromagnetic spectrum.

18. The process of claim 14, wherein the photoacoustic system further comprises an amplifier for amplifying the signal prior to the signal being transmitted.

19. The process of claim 14, wherein the signal is transmitted via radio waves.

20. The process of claim 14, wherein the signal is transmitted optically.

* * * * *